United States Patent [19]

Buck

[11] Plant 4,041

[45] Apr. 12, 1977

[54] GERANIUM PLANT NAMED MARIAN

[75] Inventor: Griffith J. Buck, Ames, Iowa

[73] Assignee: Iowa State University Research Foundation, Inc., Ames, Iowa

[21] Appl. No.: 680,153

[22] Filed: May 3, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Rummler and Snow

[57] ABSTRACT

A new geranium cultivar distinguished by its more compact and free-branching growth, its greater flowering potential, and the intensification of its pink coloring under high temperature and high light intensities. This plant blooms continuously, is tolerant of high nighttime temperatures, has good strength against breaking apart or shattering in wind or rain, and is highly resistant to *Botrytis cinerea* infection.

1 Drawing Figure

BACKGROUND OF THE NEW PLANT

My new variety of geranium plant is a seedling resulting from my cross of the unpatented variety "Galaxie" with an unnamed variety produced by my crossing the unpatented variety "Summertime" with an unnamed plant in my stock which resulted from "Pink Cloud" × "Marquise de Castellane" (both unpatented), all of which work was done by me at Iowa State University at Ames, Iowa, in the course of my extensive breeding efforts carried on at Ames, Iowa, since 1956. This new plant was discovered by me in 1972 among a group of seedlings of the first mentioned cross and was selected for propagation and test because of its apparently improved growth and blooming characteristics. Asexual propagation of this plant at Ames, Iowa, under my direction and through successive generations by means of cuttings, has demonstrated that its improved characteristics hold true from generation to generation and appear to be firmly fixed.

DESCRIPTION OF THE DRAWING

My new geranium cultivar is illustrated by the accompanying photographic drawing which shows the plant in full bloom and in full color, the colors shown being as nearly true as it is reasonable to expect from reproduction by conventional commercial photographic procedures.

DESCRIPTION OF THE NEW PLANT

The following is a description, in detail, of my new geranium plant variety with color designations according to the Horticultural Colour Chart (HCC) developed by Robert F. Wilson and published by The Royal Horticultural Society at London, England, in collaboration with the British Colour Council, the following data being from observations of plants of the new variety grown at the Iowa State University Department of Agriculture at Ames, Iowa.

THE PLANT

Origin: Seedling.

Parentage:

*Seed parent.*—Galaxie (unpatented).

*Pollen parent.*—Summertime (unpatented) × an unnamed variety resulting from Pink Cloud × Marquise de Castellane (both unpatented).

Classification:

*Botanic.*—*Pelargonium hortorum*, Bailey.

*Commercial.*—Garden geranium.

Form: Bush.

Height: 25 to 40 cm. (25 cm. as a 4 inch pot plant).

Growth: Vigorous and compact.

Habit: Sturdy, upright and free-branching.

Foliage: Abundant in quantity.

Leaves: Size — 9 to 13 cm. long.

*Shape.*—Round-cordate, with several rounded lobes and serrate margins.

*Texture.*—Firm but slightly velvety to touch.

*Color.*—Upper side — Indistinct center area of Spinach Green 0960 (HCC) with darker peripheral portions. Under side — Spinach Green 0960/2 (HCC)

*Ribs and Veins.*—Prominent on under side.

Stipules: Rounded triangular in shape and serrate.

*Size.*—0.7 to 0.9 cm. wide, 0.9 to 1.1 cm. long.

*Color.*—Scheeles Green 860/2 (HCC).

*Aspect.*—Slightly hairy.

Petioles: 10 to 14 cm. long.

Stem: Internodes are short, 1.5 to 1.8 cm. apart.

*Color.*—Scheeles Green 860/2 to 860 (HCC) as plant ages.

*Aspect.*—Slightly pubescent.

THE BUD

Size: Large; 1.1 to 1.4 cm. long, 0.6 to 0.8 cm. wide.

Shape: Pointed ovoid.

Opening: Buds open slowly.

Color: When sepals first divide — White, tinted with Rose Madder 23/3 (HCC). When petals begin to unfurl - Rose Madder 23/1 (HCC).

Sepals: Upstanding at first, later curling back.

*Shape.*—Ovate and long pointed.

*Number.*—Five separate sepals.

*Color.*—Inside — Scheeles Green 860/3 (HCC). Outside — Scheeles Green 860/2 (HCC) tinted with Rose Madder 23/1 at the base.

THE FLOWER

Blooming Habit: Continuous and abundant.

Size: Very large; 12 to 15 cm. in diameter and 5 to 7 cm. in depth.

Borne: The inflorescence is borne singly as a simple umbel.

Shape: A compact, approximately semi-globular umbel.

Florets:

*Form.*—Flat to shallow cup-shape.

*Size.*—4.3 to 4.8 cm. in diameter.

*Petals.*—6 to 8 in number. Shape: Obovate. Arrangement: Imbricated. Color: Outer petals — Rose Madder 23/1 (HCC) with a white base veined with Rose Madder 23/1. The two upper petals have a white blotch on the basal half. Reverse side — White veined and tinted Rose Madder 23/1 (HCC).

*Texture.*—Firm.

*Appearance.*—Satiny.

Petaloids: 2 to 4 in number.

*Size.*—Small; 1.1 to 1.5 cm.

*Color.*—Same as petals.

Pedicel: Length — 2.2 to 3.0 cm.

*Color.*—Scheeles Green 860/2 (HCC) tinted with Rose Madder 23/1.

*Aspect.*—Slightly hairy.

Peduncle: Sturdy and upright.

*Length.*—13 to 18 cm.

*Color.*—Scheeles Green 860/2 (HCC)

*Aspect.*—Slightly pubescent.

Effect of Hot or Wet Weather: None.

Persistence: Florets hang on and dry.

Disease Resistance: Plant is tolerant of *Botrytis cinerea.*

Lasting Quality: 7 days.

REPRODUCTIVE ORGANS

Stamens:

*Anthers.*—5 to 8 in number. Length: 0.3 cm. Arrangement: Cylindrical

*Filaments.*—0.7 to 0.9 cm. long. Color: White.

*Pollen.*—Color — Reddish-brown.

Pistils: Number — 1.

*Styles.*—1.0 to 1.2 cm. long.

*Stigma.*—Color - Red

Ovaries: 5 celled.

Fruit: Partially fertile.

*Shape.*—Ovoid with a long "beak".

*Color at Maturity.*—Brownish-black.

This geranium cultivar is similar in color to the older cultivars "Pink Jade" (unpatented), "Eleanor" (unpatented) and "Genie Irene" (unpatented) but differs from those plants in that the color intensifies under high temperatures and high light intensity. This new plant is more compact and free branching and because of its greater number of stems and a tendency to produce flowers on a consistent 2–4 node cycle, this plant has a greater flowering potential than the before mentioned varieties.

I claim:

1. A new and distinct variety of geranium plant substantially as herein shown and described, characterized by its vigorous, upright and much branched growth habit, its continuous and abundant flower production, and the tendency of its flower color to intensify under high temperature and high light conditions.

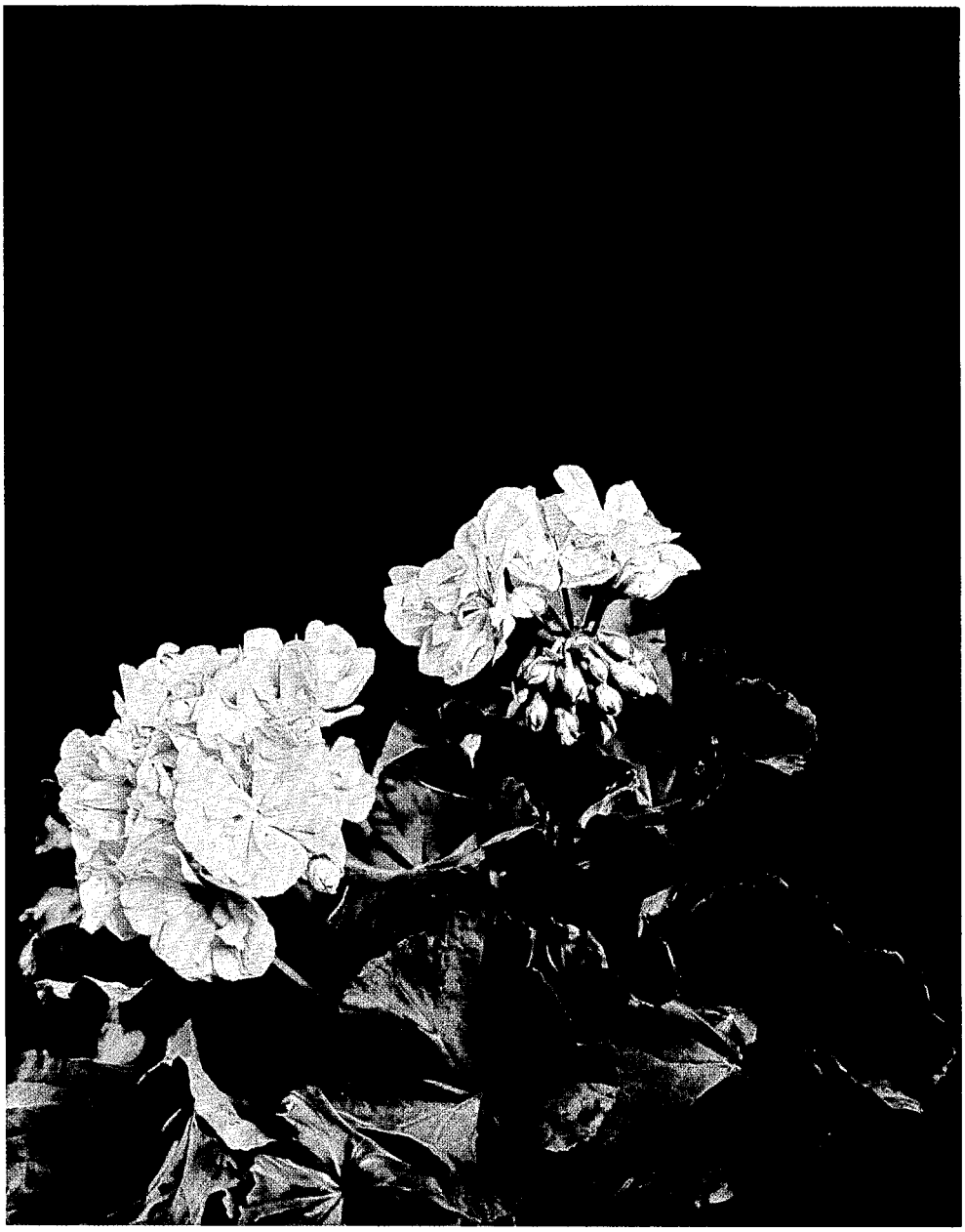

* * * * *